United States Patent [19]

Neumeier

[11] 4,004,589

[45] Jan. 25, 1977

[54] OSTOMY IRRIGATION APPARATUS

[75] Inventor: Erich Neumeier, Mosinee, Wis.

[73] Assignee: Marsan Manufacturing Company, Inc., Wausau, Wis.

[22] Filed: Nov. 10, 1975

[21] Appl. No.: 630,351

[52] U.S. Cl. .............................. 128/245; 128/283; 128/239

[51] Int. Cl.² ......................................... A61M 3/00

[58] Field of Search .......... 128/239, 244, 245, 241, 128/283, 251

[56] References Cited

UNITED STATES PATENTS

| 350,105 | 10/1886 | Bennett | 128/245 |
|---|---|---|---|
| 2,888,925 | 6/1959 | Philips | 128/251 |
| 3,765,413 | 10/1973 | Lepar | 128/283 X |
| 3,910,274 | 10/1975 | Nolan | 128/283 X |
| 3,916,897 | 11/1975 | Elmore et al. | 128/245 |

Primary Examiner—John D. Yasko
Attorney, Agent, or Firm—Merriam, Marshall, Shapiro & Klose

[57] ABSTRACT

Disclosed are ostomy irrigating devices including a truncated conical element and an apertured hollow flexible nozzle element for delivery of irrigating fluids.

14 Claims, 9 Drawing Figures

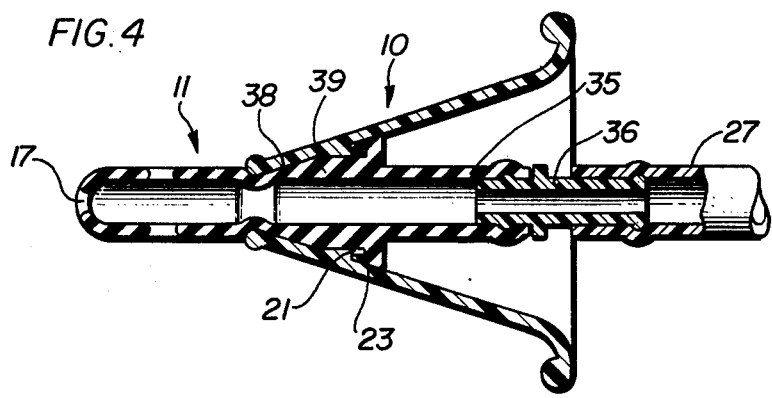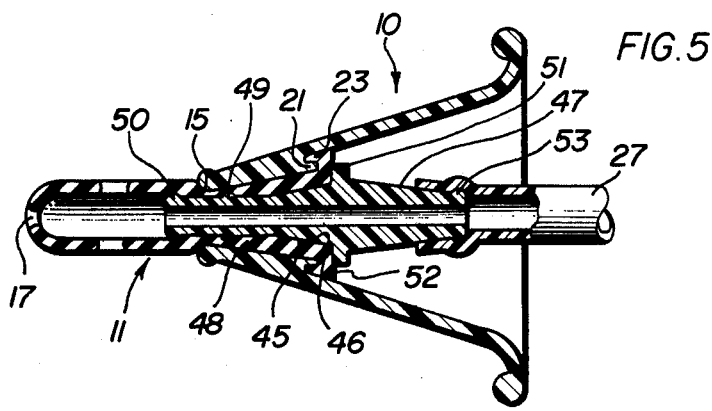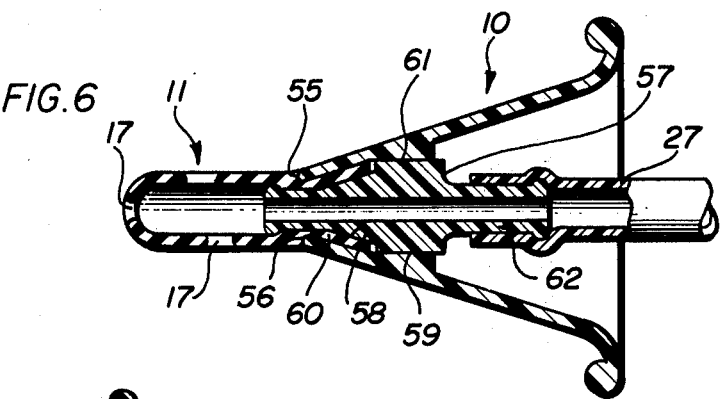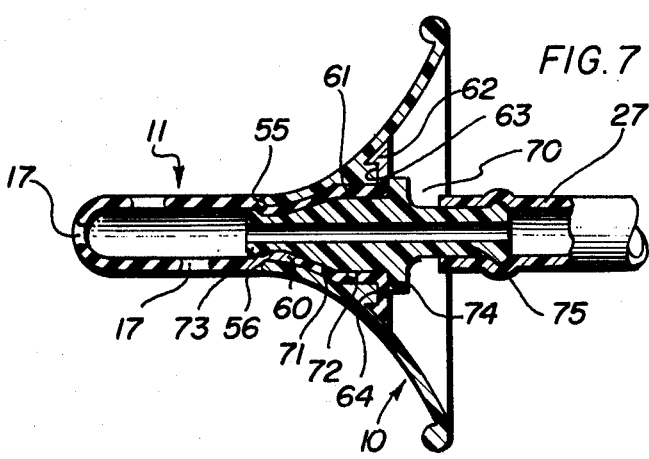

OSTOMY IRRIGATION APPARATUS

BACKGROUND OF THE INVENTION

This invention relates to medical devices. More particularly, this invention is concerned with devices useful for ostomy care.

Human surgical procedures at times require the formation on a temporary or permanent basis of an ostomy such as a colostomy or ileostomy. The waste materials from such ostomies are conventionally collected in various types of receptacles. Proper health care, however, often dictates that the intestine leading to the stoma of the ostomy be irrigated for sanitary reasons and in certain instances for the purpose of administering a medicine.

Various devices have been employed for the administration of irrigating liquids into the intestinal tract through a stoma. Thus, FIGS. 8 and 9 of the attached drawings generally show two commercial types of devices for supplying liquid into the stoma. The device shown in FIG. 8 is made of a rigid polymeric material and constitutes a conical member C and an internal tubular member D axially positioned inside of the conical member. The tubular member D joins the conical member C at its apex in an integral manner. The rear end portion E of the tubular member D has a reduced diameter for receiving an irrigating liquid supply tube. The forward end F of the conical member C is inserted into the stoma to make sealing contact therewith so that the irrigating liquid does not flow prematurely from the stoma. The rigid unyielding character of the feeding device of FIG. 8 can create discomfort where a stoma is irritated or highly sensitive.

FIG. 9 shows another prior art device for supplying irrigating liquid through a stoma. The device of FIG. 9 has a flexible polymeric elongated nozzle G which fits into the mouth of a holder H. Retainer plug I fits into the rear opening of the nozzle G and secures the nozzle into position inside of the holder H. Tube connector J is threaded into the back opening portion of the plug I and is adapted to receive a liquid supplying tube K. The device of FIG. 9 is not suitable for use in the wide range of stoma sizes because of the shape of the forward end of the holder H. In addition, it is believed quite difficult to properly insert the retainer plug I inside of the rear end of the nozzle G in a secure manner which avoids leakage.

BRIEF DESCRIPTION OF THE INVENTION

According to the present invention there is provided an ostomy irrigating device which is suitable for use in various size stoma openings for irrigating an intestinal tract. The ostomy irrigating device provided by this invention is characterized by a truncated conical walled holder having a circular open top or apex and a circular bottom. A flexible elongated hollow round-nosed nozzle, separable from the conical walled holder, and having a cylindrical front portion with at least one liquid dispensing orifice and a rear part or portion having an outwardly tapered part is supported by the holder. The nozzle front portion extends through the holder apex opening and the outwardly tapered part of the nozzle rear portion is placed in contact with an interior surface area of the holder adjacent the apex. The nozzle front portion advisably is made slightly larger than the apex opening so that a liquid seal is obtained. An additional important liquid seal is provided by the face-to-face contact of the tapered part of the nozzle with the corresponding mating tapered portion inside of the conical walled holder.

A further liquid seal is provided according to a preferred embodiment of the invention by providing a flange, on the rear part of the nozzle, which nests inside of a groove defined by a flange circularly positioned inside of the conical walled holder and spaced inwardly therefrom. The flange inside of the conical walled holder in turn nests in the groove defined by the flange on the nozzle and the nozzle wall or exterior surface.

The ostomy irrigating device of the invention is readily cleaned since the nozzle is easily separated from the conical walled holder.

The nozzle is made of a flexible material and is dimensioned to be insertable through a stoma. The flexibility of the nozzle reduces the chance of irritation of the sensitive membranes inside of the stoma. The conical walled holder, however, permits the device to adapt to stoma openings of varying sizes to permit a liquid seal therebetween.

To facilitate attaching a liquid supplying tube to the irrigating device, a tubular extension can be provided which extends backwardly from the rear of the nozzle. This extension can be integrally formed with the nozzle of the same flexible material. A rigid tube connector can be inserted into the flexible tubular extension and a hose or tube for supplying the irrigating liquid can then be attached to the other end of the rigid connector.

According to a further aspect of the invention a rigid retaining plug can be inserted at least partly into the rear opening of the nozzle to thereby compressively seal and secure the nozzle rear portion against the internal surface of the conical walled holder. A liquid supplying tube can then be removably connected to the end of the retainer plug so that irrigating liquid can be fed from the tube through the retainer plug and into the nozzle for flow into the stoma opening.

The invention will be described further in conjunction with the attached drawings, in which:

FIG. 4 is a vertical axial sectional view through a third ostomy irrigating device embodiment provided by the invention which has an integral tubular extension on the nozzle adapted for receiving a liquid supplying tube connector;

FIG. 5 is a vertical axial sectional view through a fourth embodiment of an ostomy irrigating device provided by the invention which has a retainer plug which extends into the nozzle and through the apex of the conical walled holder;

FIG. 6 shows a fifth embodiment of an ostomy irrigating device having a retainer plug having tapered and cylindrical surfaces which nest respectively with a tapered portion at the end of the nozzle and a cylindrical surface inside of the conical walled holder; and FIG. 7 shows a sixth embodiment of the invention in which a retainer plug has a centrally located lateral flange which presses against the rear surface of the nozzle.

So far as is practical, the same elements or parts which appear in the various figures of the drawings will be identified by the same numbers and will generally be described only once even though they appear in different embodiments of the invention.

Figure 1:
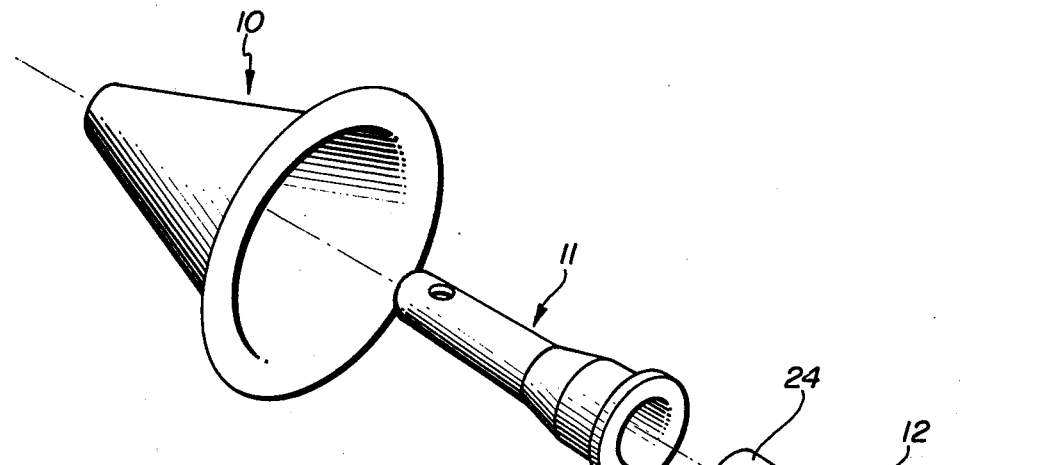
FIG. 1 is an isometric exploded view of one ostomy irrigating device provided by the invention.
Figure 2:
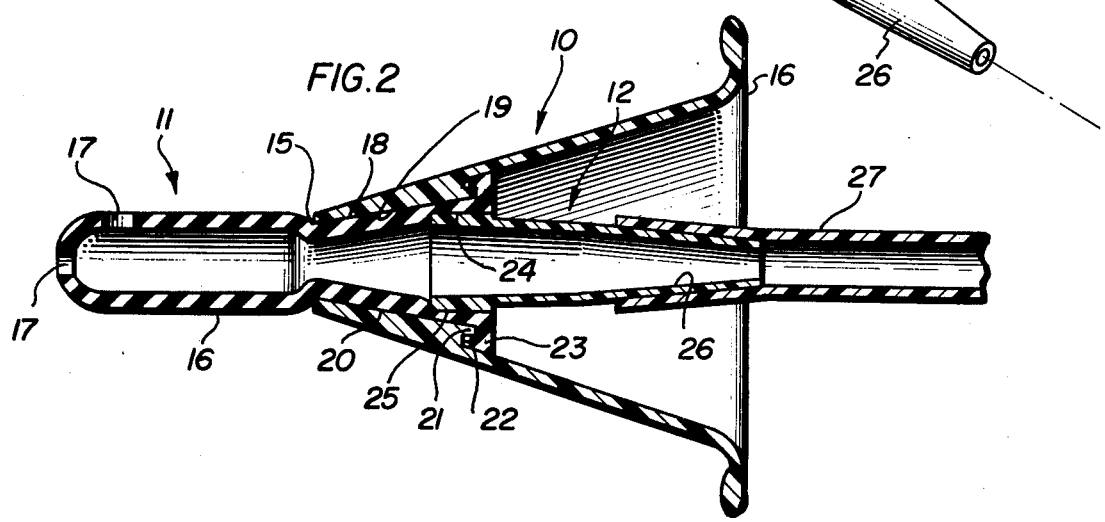
FIG. 2 is a vertical axial sectional view through the irrigating device shown in FIG. 1.

The ostomy irrigating device shown in FIGS. 1 and 2 has a truncated conical walled holder 10 with a circular open top or apex 15 and a circular bottom 16. Flexible elongated hollow round-nosed nozzle 11 has a cylindrical front portion 16 with at least one liquid dispensing orifice 17 and a rear portion 18 having an outwardly tapered part 19 in contact with the conical walled holder about an interior tapered and nesting surface 20 adjacent the apex 15. Advisably the nozzle front portion 16 is made slightly larger in circular cross-section than the interior of the circular apex 15 of the conical walled holder to thereby provide a liquid tight seal which is further reinforced by the mating sealing contact between the tapered interior surface 20 of the conical walled holder 10 and the exterior tapered surface 19 of the rear portion of the nozzle.

The conical walled holder 10 has an integral circular flange 21 projecting or extending towards the circular bottom 16 and defining a groove 22 between the flange and the internal wall of the conical holder. The tapered part 19 of the nozzle 10 has a flange 23 adapted to nest in groove 22. Furthermore, the flange 21 nests in a groove defined by the flange 23 and the tapered wall 19 of the nozzle.

To further removably retain the nozzle 11 in position in the conical walled holder 10 a retaining plug 12 can be inserted at least partly into the rear opening of the nozzle 11. The retaining plug 12 is provided with a forward cylindrical surface 24 which contacts cylindrical surface 25 located inside of the nozzle rear portion. The outer end 26 of the retaining plus 12 is tapered to facilitate slipping the end of liquid supplying tube 27 over the end of the retaining plug.

Any suitable flexible material can be used for the nozzle. For example, it can be made of natural or synthetic rubber, silicone rubber or other suitable material. Advisably, the nozzle should be made of a material which has a 40 to 90A Shore durometer range so that the desired softness and flexibility is achieved.

The conical walled holder 10 can be made of any suitable flexible, semi-flexible or rigid material. Thus, the holder can be made of low or high density polyethylene, nylon, a polyester material of the flexible type, polyvinylchloride homo and copolymers or other suitable materials. The retaining plug 12 can be made of either a polymeric material such as nylon, high density polyethylene or polypropylene or out of a metal such as aluminum or brass. It is preferred that the retaining plug be made of a rigid polymeric material.

Figure 3:
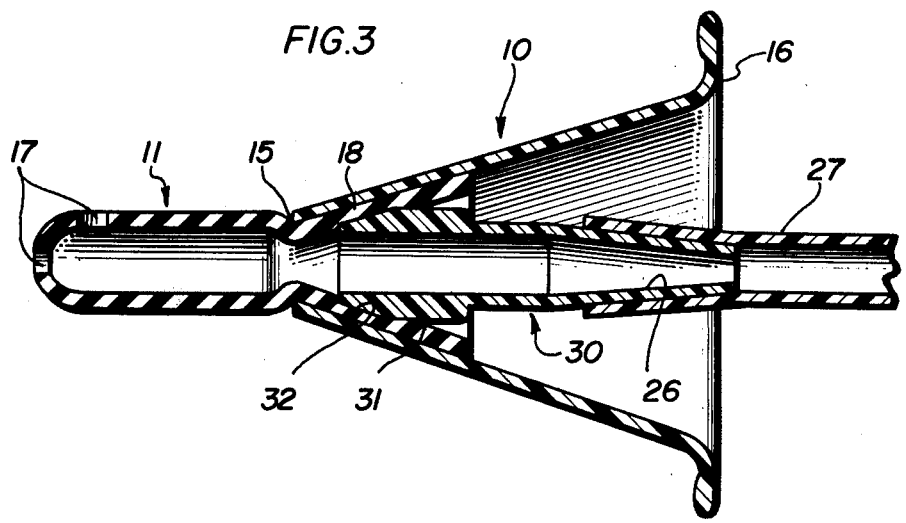
FIG. 3 is a vertical sectional view through a second ostomy irrigating device provided by the invention.
Figure 8:
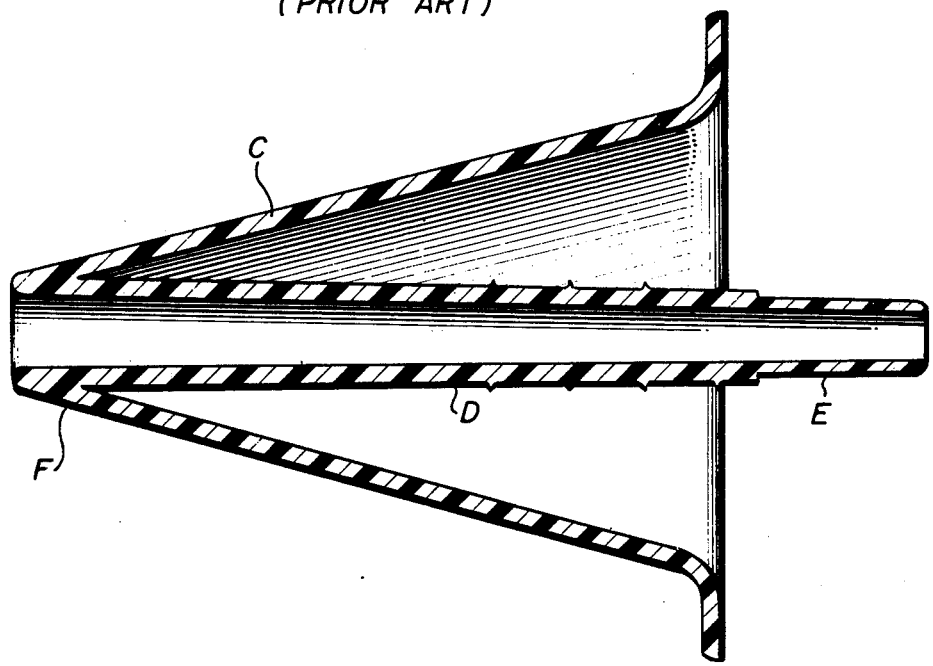
Figure 9:
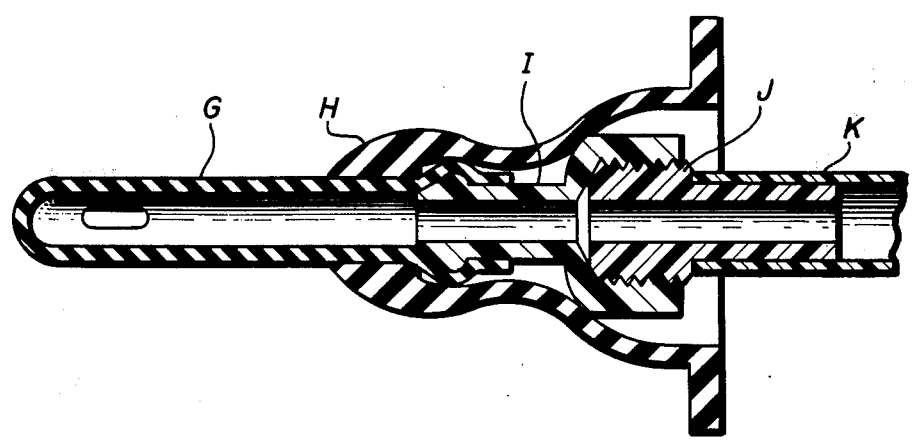

The second embodiment of the invention as illustrated by FIG. 3 shows a flexible nozzle with a tapered rear portion 18 in contact with a mating and nesting tapered surface inside of the conical walled holder 16. The retaining plug 30 shown in FIG. 3 has an enlarged forward portion 31 with a tapered nose 32 which pressably engages the inside surface of the tapered rear portion 18 of nozzle 11 to thereby removably help retain the nozzle in position inside of the conical walled holder 10.

The third enbodiment of the invention as illustrated in FIG. 4 has a nozzle 11 very much like the nozzle shown in the embodiment of FIGS. 1 and 2. However, the nozzle shown in FIG. 4 has a rearwardly projecting tubular extension 35 integrally formed as part of the nozzle. Tube connector 36 slips inside of the end of tubular extension 35 and liquid supplying tube 27 slips over the end of the connector 36. The nozzle 11 shown in FIG. 4 has a tapered portion 38 and a cylindrical portion 39 which nests with and contacts similar surfaces inside of the conical walled holder 10 to provide liquid sealing means.

The ostomy irrigating device shown in FIG. 5 has a conical walled holder 10 and a nozzle 11 quite similar to those elements shown in FIG. 2. However, the inside rearward portion of the nozzle is tapered 45 to contact and next with a similar tapered portion 46 in the retaining plug 47. The retaining plug 47 is substantially tubular and has a forward portion 48 which extends into the nozzle and through the apex 15 of the conical walled holder 10. Spaced-apart annular or ring-like elements 49 and 50 on the forward portion of retaining plug 47 serve to further hold the nozzle 11 in fixed position inside of the conical walled holder 10. An annular projecting flange 51 located about centrally on the retaining plug 47 presses against the end surface 52 of nozzle 11. This facilitates inserting the retaining plug in the nozzle and provides a limiting block to forward movement of the retaining plug. Liquid supplying tube 27 readily slips over the end 53 of the retaining plug 47.

The ostomy irrigating device shown in FIG. 6 differs from those previously described in several respects. Thus, the nozzle 11 is provided with an annular groove 55 into which the end 56 of the holder 10 fits to provide a smooth joint which avoids what could be an edge which might otherwise irritate the sensitive mucous membrane inside of an ostomy. In addition, the retaining plug 57 shown in the device of FIG. 6 has a forward tapered portion 58 and immediately behind and adjacent thereto a cylindrical portion 59. The tapered portion 58 nests with and contacts a tapered surface inside of the rear tapered part 60 of nozzle 11. The cylindrical surface 59 contacts and nests with the cylindrical internal surface 61 of conical member 10. In this way the nozzle is firmly removably positioned inside of the conical walled holder 10 and, in addition, the retaining plug 57 is firmly stabilized in position by means of the nesting arrangement between cylindrical surfaces 59 and 61. The rear tubular extension 62 on retaining plug 57 is provided for attaching liquid supplying tube 27 thereto.

A further embodiment of the invention is shown in FIG. 7. The nozzle 11 shown in this figure has a rear portion with a substantially outwardly tapered shell section 60 to which a cylindrical shell section 61 is connected. Flange 62 at the rear end of the nozzle defines a groove 63 into which flange 64, located on the inside surface of the holder 10, projects. Retaining plug 70 having an axial orifice extends inwardly through the rear portion of nozzle 11. The retaining plug 70 has a forward tapered surface 71, and a cylindrical surface 72 in back thereof, which are dimensioned to contact and nest with the nozzle tapered surface 60 and the nozzle interior cylindrical surface 61 to thereby provide a liquid seal. The forward nose 73 of the retaining plug 70 has an outwardly extending annular ridge which resiliently compresses the adjoining nozzle wall tightly against the apex portion of holder 10. Laterally extending ring or flange 74 positioned about centrally on retaining plug 70 presses against the back end of nozzle 11 and serves as a limiting block against further forward movement of the retaining plug inside of the nozzle. The rearward extending tubular projection 75 of the retaining plug 70 provides a ready means for slidably attaching the liquid feeding tube 27 thereto.

It should be noted that the holder shown in FIG. 7, instead of being precisely conical, is more or less an arcuate conical shape. This alternative shape can be used in those instances where it is desirable to make contact with the peripheral edge of the stoma without inserting a conical holder as far in as would be the case otherwise.

The foregoing detailed description has been given for clearness of understanding only, and no unnecessary limitations should be understood therefrom, as modifications will be obvious to those skilled in the art.

What is claimed is:

1. An ostomy irrigating device comprising:
   a truncated conical walled holder having a circular open top or apex and a circular bottom; and
   a flexible elongated hollow round-nosed nozzle, separable from the conical walled holder, having a cylindrical front portion with at least one liquid dispensing orifice and a rear portion having an outwardly tapered part in contact with the conical walled holder about an interior tapered surface area adjacent the apex,
   said nozzle front portion extending outwardly from the apex.

2. An ostomy irrigating device according to claim 1 in which the nozzle front portion is slightly larger in circular cross-section than the interior of the circular apex of the conical walled holder.

3. An ostomy irrigating device according to claim 1 in which the conical holder is a substantially rigid polymeric material.

4. An ostomy irrigating device according to claim 1 in which the nozzle rear portion has an integral tubular extension projecting axially outwardly.

5. An ostomy irrigating device comprising:
   a truncated conical walled holder having a circular open top or apex, a circular bottom, and an integral circular flange extending toward the circular bottom and defining a groove between the flange and the internal wall of the conical holder,
   a flexible elongated hollow round-nosed nozzle, separable from the conical walled holded, having a cylindrical front portion with at least one liquid dispensing orifice and a rear portion having an outwardly tapered part in contact with the conical walled holder about an interior tapered surface area adjacent the apex,
   said nozzle front portion extending outwardly from the apex, and
   the tapered part of the nozzle having a flange adapted to nest in the groove in the conical holder.

6. An ostomy irrigating device according to claim 5 in which the flange has an internal cylindrical surface which contacts a nozzle cylindrical surface to the rear of the nozzle tapered surface.

7. An ostomy irrigating device according to claim 6 in which the nozzle is substantially thicker walled at its cylindrical surface which contacts the holder cylindrical surface.

8. An ostomy irrigating device comprising:
   a truncated conical walled holder having a circular open top or apex and a circular bottom,
   a flexible elongated hollow round-nosed nozzle, separable from the conical walled holder, having a cylindrical front portion with at least one liquid dispensing orifice and a rear portion having an outwardly tapered part in contact with the conical walled holder about an interior tapered surface area adjacent the apex,
   said nozzle front portion extending outwardly from the apex,
   said nozzle rear portion having an integral tubular extension projecting axially outwardly, and
   a rigid hose connector inserted into the tubular extension.

9. An ostomy irrigating device comprising:
   a truncated conical walled holder having a circular open top or apex and a circular bottom,
   a flexible elongated hollow round-nosed nozzle, separable from the conical walled holder, having a cylindrical front portion with at least one liquid dispensing orifice and a rear portion having an outwardly tapered part in contact with the conical walled holder about an interior tapered surface area adjacent the apex,
   said nozzle front portion extending outwardly from the apex, and
   an elongated tubular retainer plug having a forward tapered portion inserted at least partly into the nozzle rear portion.

10. An ostomy irrigating device according to claim 9 in which the retainer plug has a flange which contacts the end of the nozzle rear portion.

11. An ostomy irrigating device comprising:
    a truncated conical walled holder having a circular open top or apex and a circular bottom,
    a flexible elongated hollow round-nosed nozzle, separable from the conical walled holder, having a cylindrical front portion with at least one liquid dispensing orifice and a rear portion having an outwardly tapered part in contact with the conical walled holder about an interior tapered surface area adjacent the apex,
    said nozzle front portion extending outwardly from the apex,
    said conical holder having an integral cylindrical surface extending beyond the end of the nozzle rear part, and
    an elongated rigid tubular retainer plug having a forward tapered portion and a cylindrical portion rearward of the tapered portion, said retainer plug being inserted at least partly into the nozzle rear portion so that the plug tapered portion fits inside the nozzle tapered portion and the plug cylindrical portion fits inside of the conical holder cylindrical surface.

12. An ostomy irrigating device according to claim 11 in which the plug has an integral tubular extension projecting axially outwardly.

13. An ostomy irrigating device according to claim 11 in which the plug has a flange which contacts the end of the nozzle rear portion.

14. An ostomy irrigating device comprising:
    a truncated conical walled holder having a circular open top or apex and a circular bottom,
    a flexible elongated hollow round-nosed nozzle, separable from the conical walled holder, having a cylindrical front portion with at least one liquid dispensing orifice and a rear portion having an outwardly tapered part in contact with the conical walled holder about an interior tapered surface area adjacent the apex,
    said nozzle front portion extending outwardly from the apex, and
    an elongated tubular retainer plug with a forward cylindrical portion is inserted into a cylindrical plug-receiving means at the rear of the nozzle.

* * * * *